United States Patent [19]
Chamberlin et al.

[11] Patent Number: 5,684,154
[45] Date of Patent: Nov. 4, 1997

[54] PROCESS FOR THE PREPARATION AND ISOLATION OF ATRACURIUM BESYLATE

[75] Inventors: Steven A. Chamberlin, Waukegan; Ashok V. Bhatia, Libertyville; Deborah A. Davis, Waukegan; Keith A. Drengler, Lindenhurst, all of Ill.

[73] Assignee: Abbott Laboratories, Abbott Park, Ill.

[21] Appl. No.: 602,945

[22] Filed: Feb. 16, 1996

[51] Int. Cl.$^6$ .................................................. C07D 217/24
[52] U.S. Cl. .......................................................... 546/140
[58] Field of Search .............................................. 546/140

[56] References Cited

U.S. PATENT DOCUMENTS 4,179,507  12/1979  Stenlake et al. .
5,453,510   9/1995  Hill et al. ................................ 546/140

OTHER PUBLICATIONS

Stenlake, J.B., et al., "Biodegradable neuromuscular blocking agents. Part 4. Atracurium Besylate and related polyalkylene di–esters", *Eur. J. Med. Chem.*, 16(6):515 524 (1981).

Stenlake, J.B., et al., "Biodegradable neuromuscular blocking agents. Part 6. Stereochemical studies on atracurium and related polyalkylene di–esters", *Eur. J. Med. Chem.*, 19(5):441–450 (1984).

*Primary Examiner*—Patricia L. Morris
*Attorney, Agent, or Firm*—Michael J. Ward

[57] ABSTRACT

A process of producing atracurium besylate that substantially reduces the level of impurities in the final product and avoids the repeated use of ether is provided. In accordance with such a process, N, N'-4,10-dioxa-3,11-dioxotridecylene-1,13-bis-tetrahydropapaverine (Compound 1), methyl benzenesulfonate and a catalytic amount of an insoluble base in a solvent are combined to form a reaction mixture that is maintained for a period of time sufficient for atracurium besylate formation. The reaction mixture is then filtered to remove the insoluble base and the atracurium besylate is precipitated.

27 Claims, No Drawings

PROCESS FOR THE PREPARATION AND ISOLATION OF ATRACURIUM BESYLATE

TECHNICAL FIELD OF THE INVENTION

This invention relates to a process for the preparation and isolation of atracurium besylate.

BACKGROUND OF THE INVENTION

Existing methods of producing atracurium besylate involve the reaction of N, N'-4,10-dioxa-3,11-dioxotridecylene-,13-bis-tetrahydropapaverine, [CAS registry number 64228-77-9], hereinafter referred to as Compound 1 with methyl benzenesulfonate to provide the bis-quaternary ammonium product (atracrium besylate). A major shortcoming of existing methods is the incomplete reaction of starting materials resulting in a product containing up to 1.5% of incompletely converted Compound 1. Removal of the incompletely converted Compound 1 from the desired product is difficult.

Another problem of existing methods is the removal of residual methyl benzenesulfonate from the desired product. Methyl benzenesulfonate is removed in existing methods by redissolving the crude product, obtained by precipitation with diethyl ether, in a suitable solvent such as acetonitrile and reprecipitating with diethyl ether. The purification by ether precipitation is inefficient and may need to be repeated 3 to 4 times to reduce the methyl benzenesulfonate to acceptably low levels. An improved purification method would require fewer operations and avoid the hazards associated with large-scale use of diethyl ether.

There continues to be a need for a method of producing atracurium besylate with improved product purity in an efficient manner which avoids the use of diethyl ether.

BRIEF SUMMARY OF THE INVENTION

The present invention provides a process of producing atracurium besylate, 2,2'-[1,5-pentanediylbis-[oxy(3-oxo-3,1-propanediyl)]]bis[1-[3,4-dimethoxyphenyl)-methyl]-1,2,3,4-tetrahydro-6,7-dimethoxy-2-methylisoquinolinium ] dibenzenesulfonate, wherein Compound 1, methyl benzenesulfonate and a catalytic amount of an insoluble base in a solvent are combined to form a reaction mixture that is maintained for a period of time sufficient for atracurium besylate formation. The reaction mixture is then filtered to remove the insoluble base and then the atracurium besylate is precipitated and collected.

DETAILED DESCRIPTION OF THE INVENTION

The present invention relates to a process of producing atracurium besylate that substantially reduces the level of impurities in the final product. In accordance with such a process, Compound 1, methyl benzenesulfonate and a catalytic amount of an insoluble base are combined to form a reaction mixture that is maintained for a period of time sufficient for atracurium besylate formation. The reaction mixture is then filtered to remove the insoluble base, followed by subsequent atracufium besylate precipitation and collection.

Another embodiment of the present invention incindes forming a reaction mixture comprising, Compound 1, methyl benzenesulfonate and a catalytic amount of an insoluble base in a solvent. Suitable solvents include, but is not intended to be limited to, acetonitrile. The reaction mixture is maintained for a period of time sufficient for atracurium besylate formation. The reaction mixture may then be filtered to remove the insoluble base and the atracurium besylate may be precipitated by diluting with an aromatic hydrocarbon with or without alcohol, and adding to a solution comprising an acetate and a lower aliphatic hydrocarbon. Acetates suitable include, but are not intended to be limited to, ethyl acetate, isopropyl acetate, and methyl acetate. Lower aliphatic hydrocarbons suitable include, but are not intended to be limited to, heptane, hexane, and pentane. In an alternative embodiment, tert-butyl methyl ether (MTBE) may be substituted for the solution of acetate and a lower aliphatic hydrocarbon.

The use of an insoluble base in the reaction mixture has the advantage of driving the reaction to completion leading to a purer product. The use of aromatic hydrocarbons with or without an alcohol and an acetate and and a lower aliphatic hydrocarbon has the advantage of avoiding the use of diethyl ether on a large scale for the isolation of the product and reducing the number of precipitations required to purify the bulk drug.

Compound 1, or atracurium besylate containing incompletely converted Compound 1, may be dissolved in a solution of acetonitrile and methyl benzenesulfonate at a weight:weight:weight ratio of about 1:0.5–1.5:1.5–2.5, respectively. An insoluble base, including but not intended to be limited to inorganic carbonate and bicarbonates, is added to the reaction mixture at a weight ratio of from about 1.0 to about 50.0 milligram (mg) per gram of atracurim, more preferably from about 1.0 to about 20.0 mg per gram of atracurim, and most preferably from about 2.5 to about 10.0 mg base per gram of atracurium. Inorganic carbonates include, but are not limited to potassium carbonate, calcium carbonate, sodium carbonate, and lithium carbonate. A preferred inorganic, insoluble carbonate base is sodium carbonate. The reaction mixture is maintained, with stirring, until the reaction is complete. Atracurium besylate is precipitated from the reaction mixture and collected. In a preferred embodiment, the reaction mixture is filtered to remove the insoluble base prior to precipitation.

In one embodiment of the present invention, precipitation of atracurium besylate may be accomplished by diinting the reaction mixture with an aromatic hydrocarbon. Aromatic hydrocarbons which can be used with the present invention include, but are not intended to be limited to, benzene, xylene and toluene. A most preferred aromatic hydrocarbon is toluene.

Yet another embodiment of the present invention utilizes precipitation by diluting with both an alcohol and an aromatic hydrocarbon. Alcohols which can be used with the present invention include, but are not intended to be limited to, methanol, ethanol, 1-propanol, 1-butanol, 2-butanol,iso-butanol, and tert-butanol. When an alcohol is used to dilute with an aromatic hydrocarbon, the ratio of alcohol and aromatic hydrocarbon to atracurium in the reaction mixture depends upon the particular alcohol and hydrocarbon used. A most preferred alcohol is isopropanol. Where the alcohol is isopropanol, a preferred ratio is from about 0.5 to about 5 grams of isopropanol per gram of atracurium, and a more preferred ratio of from about 1.0 to about 1.5 grams of isopropanol per gram of atracurium. Where the aromatic hydrocarbon is toluene, a preferred ratio is about from about 5 to about 15 grams of toluene per gram of atracurium, and a more preferred ratio is about from about 7 to about 10 grams of toluene per gram of atracurium.

The diluted reaction mixture is then added slowly to a solution containing an acetate and a lower aliphatic hydrocarbon. Examples of acetates suitable are ethyl acetate, isopropyl acetate, or methyl acetate. Suitabler lower aliphatic hydrocarbons, include but are not intended to be limited to, heptane, penlane or hexane. A preferred acetate is ethyl acetate and a preferred lower aliphatic hydrocarbon is heptane. A preferred ratio of ethyl acetate is from about 25 to about 100 grams of ethyl acetate per gram of atracurium, and a more preferred ratio is about from about 50 to about 100 grams of ethyl acetate per gram of atracurium. For heptane, a preferred ratio is from about 5 to about 25 grams of heptane per gram of atracurium, and a more preferred ratio is about from about 5 to about 15 grams of heptane per gram of atracurium. The solid (precipitated atracurium besylate) is then collected. Collection includes the steps of riteting the reaction mixture, washing the retained material with a solvent such as, but not intended to be limited to, toluene and heptane, and drying the washed material under nitrogen.

Any residual methyl benzenesulfonate present in the final product may be removed by reprecipitating the collected product. The reprecipitation may be carded out in similar fashion to the initial precipitation although the ratios of solvents may vary due to less methyl benzenesulfonate being present. The product may be dissolved in a reprecipitation solution, such as acetonitrile with an an aromatic hydrocarbon with or without an alcohol. A preferred alcohol is isopropanol and a preferred hydrocarbon is toluene.

Preferred ratios of acetonitrile, isopropanol and. toluene to atracurium are from about 0.5 to about 1.0 gram of acetonitrile, from about 1 to about 2 grams of isopropanol and from about 5 to about 10 grams of toluene per gram of atracurium. The reprecipitation solution is then added slowly to a solution of acetate, such as ethyl acetate (from about 40 to about 50 grams per gram of atracurium) and a lower aliphatic hydrocarbon, such as heptane (from about 5 to about 10 grams per gram atracurium). In an alternative embodiment, tert-butyl methyl ether (MTBE) may be substituted for the solution of acetate and a lower aliphatic hydrocarbon. If necessary, the reprecipitation can be repeated until the level of residual methyl benzenesulfonate is reduced to an acceptable level.

The following Examples illustrate embodiments of the present invention and are not limiting of the specification and the claims in any way.

EXAMPLE 1: Preparation of Atracurium Besylate

Compound 1 (20 grams (gm)), acetonitrile (24 gm), methyl benzenesulfonate (48 gin), and sodium carbonate (0.05 gm) were combined and stirred at ambient temperature. After 17 hours the mixture was filtered, then diluted with isopropanol (30 milliliters (mL)) and toluene (200 mL). The mixture was charged to 5:1 ethyl acetate/heptanes (ethyl acetate/heptane volume of 1.8 L) resulting in a flocculent precipitate. The solids were collected and washed with toluene (300 mL) and heptanes (300 mL). Drying on the filter under a nitrogen stream for one hour afforded the crude atracurium besylate as a free-flowing, slightly off-white powder.

The crude product was dissolved in acetonitrile (11 gm), isopropanol (27 gm), and toluene (60 gm), then diluted with an additional volume of toluene (130 mL). Precipitation of the desired product by dropwise addition of this solution to to 5:1 ethyl acetate/heptanes (ethyl acetate/heptane volume of 1.2 L) was followed by collection of the solids and washing as above. The dried atracurium besylate (16.7 gm, 72%) was found to have <0.1% residual methyl benzenesulfonate, and a purity of greater than 98% by HPLC.

EXAMPLE 2 Effects of the Ratio of Solvents to Residual Methyl Benzenesulfonate in the Final Product Studies were performed to determine the effect of varying the ratio of solvents on the amount of residual methyl benzenesulfonate (MeOBs) in the product obtained after precipitation. In these studies, the reaction mixture was diluted with isopropanol (IPA) and toluene (Tol) in the ratios shown below, then added to ethyl acetate and heptane (5:1 ethyl acetate/heptane), filtered, washed with toluene, and then heptane.

The reaction mixture contained Compound 1, methyl benzenesulfonate and acetonitrile in a weight (gram) ratio of 1:2:0.5. The results are summarized below in Table 1. The Peak Area Percent (PA%) is the absorbance of ultraviolet light at 265 nanometers (nm) as determined by HPLC.

TABLE 1

| (IPA:Tol:EA-Hept)/Compound 1 (ml/gram) | % MeOBs (PA % 265 nm) |
|---|---|
| (2:10:60) | 0.7 |
| (1.5:6.50) | 1.7 |
| (1.5:6:50) | 2.7–3.2 |
| (1.5:10:60) | 1.0 |

EXAMPLE 3: Effects of Reprecipitation on ReSidual MeOBs

Products obtained from the studies in Example 2 were reprecipitated once by diluting the product with 2 mL of isopropanol and 10 mL of toluene (per gram of isolated solids of atracurium besylate) and analyzed for methyl benzenesulfonate levels. The toluene was heated to a temperature of 50° C.–70° C. prior to dilution. The diluted sample was then added dropwig to 50 mL of a 5:1 (v/v) solution of ethyl acetate and heptane. The results of these studies are summarized below in Table 2.

TABLE 2

| % MeOBs before reprecipitation | % MeOBs in final product |
|---|---|
| 3.1 | <0.1 |
| 1.7 | <0.1 |
| 2.7–3.2 | <0.1 |
| 1.6 | <0.1 |

EXAMPLE 4: Removal of Methyl Benzenesulfonate from Atracurium Besylate by Reprecipitation in MTBE Crude atracurium besylate (1.0 gm) containing 6.5% methyl benzenesulfonate (HPLC peak area percent, 265 nm) was dissolved in ethanol (3 mL) and toluene (25 mL). The solution was added dropwise to tert-butyl methyl ether (MTBE)(40 mL). The resulting solids were washed with MTBE followed by heptane. HPLC of the dried solids showed 0.5% residual methyl benzenesulfonate. The collected solids were reprecipitated by the procedure described in this example and found to have <0.1% residual methyl benzenesulfonate.

EXAMPLE 5: Rework of atracurium besylate containing incompletely reacted Compound 1

Atracurium besylate containing 1.3% (HPLC peak area percent, 280 nm) Compound 1 was dissolved in acetonitrile and methyl benzenesulfonate. To this solution was added potassium carbonate and the reaction mixture was stirred for 16 hours. The reaction mixture was found to be free of Compound 1 and partially convened Compound 1.

What is claimed is:

1. A process of making, 2,2'-[1,5-pentanediylbis-[oxy(3-oxo-3,1-propanediyl)]]bis[1-[3,4-dimethoxyphenyl)-methyl ]-1,2,3,4-tetrahydo-6,7-dimethoxy-2-methlisoquinolinium] dibenzenesulfonate, comprising the steps of:
   (a) combining N, N'-4,10-dioxa-3,11-dioxotridecylene-1,13-bis-tetrahydro-papaverine, methyl benzenesulfonate and a catalytic amount of an insoluble base to form a reaction mixture and
   b) precipitating, 2,2'-[1,5-pentanediylbis-[oxy(3-oxo-3,1-propanediyl)]]bis[1-[3,4-dimethoxyphenyl)-methyl]-1,2,3,4-tetrahydo-6,7-dimethoxy-2-methylisoquinolinium] dibenzenesulfonate.

2. A process of claim 1 wherein step (a) further comprises adding a solvent.

3. A process of claim 2 wherein said solvent is acetonitrile.

4. A process of claim 1 wherein, 2,2'-[1,5-pentanediylbis-[oxy (3-oxo-3,1-propanediyl)]]bis[1-[3,4-dimethoxyphenyl)-methyl]-1,2,3,4-tetrahydo-6,7-dimethoxy-2-methlisoquinolinium] dibenzenesulfonate, is precipitated in step (b) by diluting the filtered reaction mixture with an aromatic hydrocarbon.

5. A process of claim 4 wherein said diluted reaction mixture is added to a solution comprising an acetate and a lower aliphatic hydrocarbon.

6. A process of claim 4 wherein an alcohol is added to dilute the reaction mixture.

7. A process of claim 6 wherein said alcohol is selected from the group consisting of: methanol, ethanol, 1-propanol, 1-butanol, 2-butanol, iso-butanol, tert-butanol and isopropanol.

8. A process of claim 4 wherein the aromatic hydrocarbon is selected from the group consisting of: benzene, xylene, and toluene.

9. A process of claim 5 wherein said acetate is selected from the group consisting of: ethyl acetate, isopropyl acetate, and methyl acetate.

10. A process of claim 5 wherein said lower aliphatic hydrocarbon is selected from the group consisting of: heptane, hexane, and pentane.

11. A process of claim 1 wherein said collecting of precipitated, 2,2'-[1,5-pentanediylbis-[oxy(3-oxo-3,1-propanediyl)]]bis [1-[3,4-dimethoxyphenyl)-methyl]-1,2,3,4-tetrahydo-6,7-dimethoxy-2-methylisoquinolinium] dibenzenesulfonate, comprises the steps of:
   (a) filtering the precipitated,2,2'-[1,5-pentanediylbis-[oxy (3-oxo-3,1-propanediyl)]]bis[1-[3,4-dimethoxyphenyl)-methyl ]-1,2,3,4-tetrahydo-6,7-dimethoxy-2-methylisoquinolinium] dibenzenesulfonate;
   (b) washing the precipitated,2,2'-[1,5-pentanediylbis-[oxy (3-oxo-3,1-propanediyl) ]]bis[1-[3,4-dimethoxyphenyl)-methyl]-1,2,3,4-tetrahydo-6,7-dimethoxy2-methlisoquinolinium] dibenzenesulfonate, with at least one solvent selected from the group consisting of: toluene and heptane; and
   (c) drying the washed precipitated,2,2'-[1,5-pentanediylbis-[oxy (3-oxo-3,1-propanediyl) ]]bis[1-[3,4-dimethoxyphenyl)-methyl]-1,2,3,4-tetrahydo-6,7-dimethoxy-2-methlisoquinolinium] dibenzenesulfonate.

12. A process of claim 11 further including the step of reprecipitating the, 2,2'-[1,5-pentanediylbis-[oxy(3-oxo-3,1-propanediyl)]]bis[1-[3,4-dimethoxyphenyl)-methyl]-1,2,3,4-tetrahydo-6,7-dimethoxy-2-methylisoquinolinium] dibenzenesulfonate.

13. The process of claim 12 wherein reprecipitating, 2,2'-[1,5-pentanediylbis-[oxy(3-oxo-3,1-propanediyl)]]bis [1-[3,4-dimethoxyphenyl)-methyl ]-1,2,3,4-tetrahydo-6,7-dimethoxy-2-methlisoquinolinium] dibenzenesulfonate, comprises the steps of:
   (a) dissolving the washed,2,2'-[1,5-pentanediylbis-[oxy (3-oxo-3,1-propanediyl)]]bis[1-[3,4-dimethoxyphenyl)-methyl ]-1,2,3,4-tetrahydo-6,7-dimethoxy-2-methylisoquinolinium] dibenzenesulfonate, in a solution comprising acetonitrile and an aromatic hydrocarbon and
   (b) reprecipitating with an acetate and a lower aliphatic hydrocarbon.

14. The process of claim 12 further comprising an alcohol to dissolve the washed, 2,2'-[1.5-pentanediylbis-[oxy(3-oxo-3,1-propanediyl)]]bis[1-[3,4-dimethoxyphenyl)-methyl ]-1,2,3,4-tetrahydo-6,7-dimethoxy-2-methylisoquinolinium] dibenzenesulfonate.

15. The process of claim 13 wherein said reprecipitation is accomplished with tert-butyl methyl ether.

16. The process of claim 6 wherein the alcohol is isopropanol and the aromatic hydrocarbon is toluene.

17. The process of claim 1 wherein the weight ratio of N, N'-4,10-dioxa-3,11-dioxotridecylene -bis- tetrahydropapaverine, acetonitrile and methyl benzenesulfonate is about 1.0: 0.5–1.5:1.5–2.5 respectively.

18. A process of claim 1 wherein said insoluble base is present in said reaction mixture in the range of about 2.5 to about 10.0 milligrams per gram of N,N'-4,10-dioxa-3,11-dioxotridecylene-1,13-bis-tetrahydropapaverine.

19. A process of claim 1 wherein said insoluble base is inorganic carbonates and bicarbonates.

20. A process of claim 19 wherein said insoluble base is selected from the group consisting of: potassium carbonate, calcium carbonate, sodium carbonate, and lithium carbonate.

21. The process of claim 1 wherein the reaction mixture is diluted with an alcohol in an amount in the range of about 0.5 to about 5 grams per gram of N, N'-4, 10-dioxa-3,11-dioxotridecylene-1,13-bis-tetrahydropapaverine.

22. A process of claim 21 wherein said alcohol is isopropanol.

23. The process of claim 1 wherein the reaction mixture is diluted with an aromatic hydrocarbon in an amount in the range of about 5.0 to about 15 grams per gram of N, N'-4,10-dioxa-3,11-dioxotridecylene-1,13-bis-tetrahydropapaverine.

24. The process of claim 23 wherein said aromatic hydrocarbon is toluene.

25. A process of claim 13 wherein said acetate is ethyl acetate in an amount in the range of from about 25 to about 100 grams per gram of, 2,2'-[1,5-pentanediylbis-[oxy(3-oxo-3,1-propanediyl) ]]bis[1-[3,4-dimethoxyphenyl)-methyl]-1,2,3,4-tetrahydo-6,7-dimethoxy-2-methylisoquinolinium] dibenzenesulfonate.

26. A process of claim 13 wherein said lower aliphatio hydrocarbon is heptane in an amount in the range of from about 5.0 to about 25.0 grams per gram of, 2,2'-[1,5-pentanediylbis-[oxy(3-oxo-3,1-propanediyl)]]bis[1-[3,4-dimethoxypbenyl)-methyl]-1,2,3,4-tetrahydo-6,7-dimethoxy-2-methylioquinolinium] dibenzenesulfonate.

27. The process of claim 13 wherein acetonitrile is added to said reaction mixture in an amount from about 0.5 to about 1.0 grams of acetonitrile per gram of, 2,2'-[1,5-pentanediylbis-[oxy(3-oxo-3,1-propanediyl)]]bis[1-[3,4-dimethoxyphenyl)-methyl ]-1,2,3,4-tetrahydo-6,7-dimethoxy-2-methylisoquinolinium] dibenzenesulfonate.

* * * * *

UNITED STATES PATENT AND TRADEMARK OFFICE
CERTIFICATE OF CORRECTION

PATENT NO. : 5,684,154

DATED : November 4, 1997

INVENTOR(S) : Steven A. Chamberlin, et al

It is certified that error appears in the above-identified patent and that said Letters Patent is hereby corrected as shown below:

In column 1, line 60 delete [atracufium] and insert --- atracurium ---.

In column 1, line 62 delete [incindes] and insert --- includes ---.

In column 2, line 41 delete [diinting] and insert --- diluting ---.

In column 2, line 52 delete [-butanol,iso-] and insert --- -butanol, iso- ---.

In column 3, line 4 delete [penlane] and insert --- pentane ---.

In column 3, line 14 delete [riteting] and insert --- filtering ---.

In column 3, line 20 delete [carded] and insert --- carried ---.

UNITED STATES PATENT AND TRADEMARK OFFICE
CERTIFICATE OF CORRECTION

PATENT NO. : 5,684,154
DATED : November 4, 1997
INVENTOR(S) : Steven A. Chamberlin, et al.

It is certified that error appears in the above-identified patent and that said Letters Patent is hereby corrected as shown below:

In column 3, line 47 delete [48 gin] and insert --- 48 gm ---.

In column 4, line 29 delete [ReSidual] and insert --- residual ---.

In column 5, line 4 delete [convened] and insert --- converted ---.

In column 6, line 54 delete [aliphatio] and insert --- aliphatic ---.

Signed and Sealed this

Fifth Day of May, 1998

*Attest:*

BRUCE LEHMAN

*Attesting Officer*  *Commissioner of Patents and Trademarks*